(12) United States Patent
Araldi et al.

(10) Patent No.: US 7,563,797 B2
(45) Date of Patent: Jul. 21, 2009

(54) SUBSTITUTED IMIDAZO(1,2-A)PYRIMIDINES AND IMIDAZO(1,2-A) PYRIDINES AS CANNABINOID RECEPTOR LIGANDS

(75) Inventors: Gian-Luca Araldi, East Setauket, NY (US); Matthew Ronsheim, Port Jefferson, NY (US); Nhut K. Diep, Hauppauge, NY (US)

(73) Assignee: Forest Laboratories Holding Limited (BM)

( * ) Notice: Subject to any disclaimer, the term of this patent is extended or adjusted under 35 U.S.C. 154(b) by 0 days.

(21) Appl. No.: 11/845,117

(22) Filed: Aug. 27, 2007

(65) Prior Publication Data

US 2008/0058350 A1  Mar. 6, 2008

Related U.S. Application Data

(60) Provisional application No. 60/823,691, filed on Aug. 28, 2006.

(51) Int. Cl.
*C07D 487/04* (2006.01)
*A61K 31/519* (2006.01)
*A61P 19/10* (2006.01)
*A61P 19/02* (2006.01)
*A61P 25/02* (2006.01)
*A61P 37/02* (2006.01)

(52) U.S. Cl. ............... 514/259.1; 514/259.5; 514/300; 544/281; 546/121

(58) Field of Classification Search ........... 544/281; 514/259.1, 259.5
See application file for complete search history.

(56) References Cited

U.S. PATENT DOCUMENTS

| | | | |
|---|---|---|---|
| 3,746,743 | A | 7/1973 | Mehta et al. |
| 5,614,531 | A | 3/1997 | Juraszyk et al. |
| 6,248,755 | B1 | 6/2001 | Chapman et al. |
| 6,358,971 | B1 | 3/2002 | Ezquerra-Carrera et al. |
| 7,176,242 | B2 | 2/2007 | John et al. |
| 7,196,095 | B2 | 3/2007 | Biftu et al. |
| 2006/0040940 | A1 | 2/2006 | Bettati et al. |
| 2006/0106020 | A1 | 5/2006 | Rodgers et al. |

FOREIGN PATENT DOCUMENTS

BE  620141  5/1962

(Continued)

OTHER PUBLICATIONS

Vippagunta et. al. (Advanced Drug Delivery Reviews, 2001, 48, pp. 3-26).*
International Search Report for PCT/US2007/076839, mailed Sep. 17, 2008.
Written Opinion of the International Searching Authority for PCT/US2007/076839, mailed Sep. 17, 2008.
STN Printout for JP 61-056180 A, Mar. 20, 1986.
Fabrichnyi et al., A New Synthesis of 2,3,4,5-Tetradehydrobiotin, Translated from Doklady Akademii Nauk SSSR, vol. 162, No. 1, pp. 120-123, May 1965.
Ferrari et al., Studi Nella Serie Della Pyridina, Nota V—Acidi imidazo-[1,2α]piridincarbossilici, Il Farmaco—Ed. Sc.—vol. XVII—fasc. 8, pp. 611-620, 1962.
Ferrari et al., Studi Nella Serie Della Pyridina, Nota VI—Amidi ed esteri imidazo—[1,2α]piridincarbossilici, Il Farmaco—Ed. Sc.—vol. XVIII—fasc. 1, pp. 42-46, 1962.

(Continued)

*Primary Examiner*—Brenda L Coleman
*Assistant Examiner*—Susanna Moore
(74) *Attorney, Agent, or Firm*—Michael Ciraolo, Esq.

(57) ABSTRACT

The present invention relates to compounds of formula I, II, III or IV:

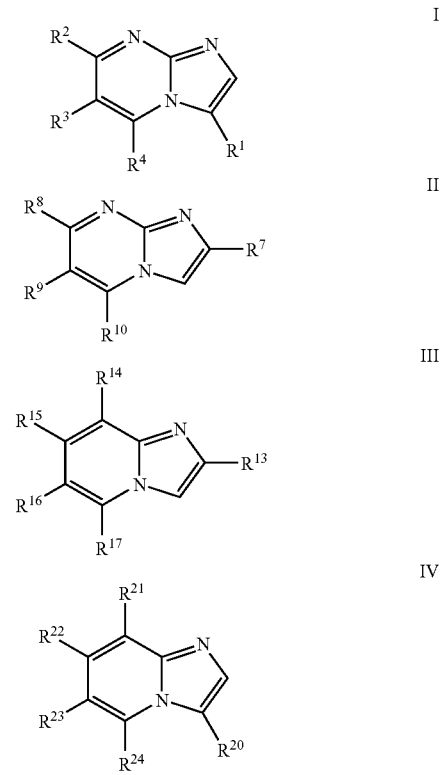

wherein $R^1$-$R^4$, $R^7$-$R^{10}$, $R^{13}$-$R^{17}$ and $R^{20}$-$R^{24}$ are as described herein. The compounds are active as cannabinoid receptor ligands, e.g., CB2 ligands. Methods of preparing the compounds, compositions containing the compounds and methods of treatment using the compounds are also disclosed.

10 Claims, No Drawings

FOREIGN PATENT DOCUMENTS

| | | |
|---|---|---|
| CH | 590 862 | 6/1977 |
| DE | 1192657 | 5/1965 |
| FR | 2510576 A1 | 2/1983 |
| JP | 61-056180 A | 3/1986 |
| JP | 3477238 | 9/2003 |
| JP | 2003-313126 | 11/2003 |
| JP | 2004-2826 | 1/2004 |
| JP | 2005-343889 | 12/2005 |
| NL | 6409696 | 2/1965 |
| WO | WO 02/34748 | 5/2002 |
| WO | WO 02/066477 | 8/2002 |
| WO | WO 02/066478 | 8/2002 |
| WO | WO 03/048132 | 6/2003 |
| WO | WO 2004/021989 | 3/2004 |
| WO | WO 2005/023759 | 3/2005 |
| WO | WO 2005/107762 | 11/2005 |
| WO | WO 2006/044509 | 4/2006 |
| WO | WO 2006/049339 | 5/2006 |
| WO | WO 2006/088246 | 8/2006 |
| WO | WO 2006/114261 | 11/2006 |
| WO | WO 2007/022529 | 2/2007 |
| WO | WO 2007/034282 | 3/2007 |
| WO | WO 2007/056469 | 5/2007 |
| WO | WO 2007/086080 | 8/2007 |
| WO | WO 2007/096764 A2 | 8/2007 |

OTHER PUBLICATIONS

Fisher et al., Imidazol[1,2-α]pyridine Anthelmintic and Antifungal Agents, Journal of Medicinal Chemistry, 1972, vol. 15, No. 9, 982-985, 1971.

Marchetti et al., Azione Diuretica Di Alcuni Derivati Degli Acidi Fenilimidazopiridincarbossilici, Il Farmaco—Ed. Sc.—vol. XVIII—fasc. 4, pp. 275-287, 1962.

Otto Dann, et al., Trypanocide Daimidine mit drei Ringen in zwei isolierten Ringsystemen, Liebigs Ann. Chem. 760, 37-87 (1972).

Tomoda et al., Substituent Effects on Fluorescent Properties of Imidazol[1,2-α]pyridine-Based Compounds, Bull. Chem. Soc. Jpn., 72, 1327-1334 (1999).

Tsuge, et al. A Novel Tetravalent Sulfur Compound, 1,3,6-Triphenylimidazo[1,2-c]thia$^{IV}$zole; Synthesis and Peripheral Cycloaddition Reaction, The Chemical Society of Japan, Chemistry Letters, pp. 1491-1494, 1982.

\* cited by examiner

SUBSTITUTED IMIDAZO(1,2-A)PYRIMIDINES AND IMIDAZO(1,2-A) PYRIDINES AS CANNABINOID RECEPTOR LIGANDS

This application claims the benefit of U.S. Provisional Application Ser. No. 60/823,691, filed Aug. 28, 2006, the entire disclosure of which is hereby incorporated by reference.

FIELD OF THE INVENTION

The present invention relates to imidazopyridine and imidazopyrimidine derivatives that act as cannabinoid receptor ligands, e.g., CB2 ligands. The invention also relates to methods of preparing the compounds, compositions containing the compounds, and to methods of treatment using the compounds.

BACKGROUND OF THE INVENTION

Cannabinoids are a specific class of psychoactive compounds present in *Cannabis sativa*. Cannabinoids are known to affect various systems and/or organs, the most important being the central nervous system and the cardiovascular system. Effects of cannabinoid intake include alterations in memory and cognition, euphoria and sedation. Cannabinoids also increase heart rate and vary systemic arterial pressure. Peripheral effects related to bronchial constriction, immunomodulation, and inflammation have also been observed. The ability of cannabinoids to reduce intraocular pressure and to affect respiratory and endocrine systems is also well known.

There are two main types of cannabinoid receptors, CB1 which is expressed mainly in the basal ganglia and the limbic system of the brain, the lungs, liver and kidneys and CB2 which is mainly expressed on T cells of the immune system and in hematopoietic cells.

Compounds that are agonists or antagonists of one or both of the cannabinoid receptors have been shown to provide a variety of pharmacological effects. See, e.g., Pertwee, R. G., PHARMACOL. THER., 74:129-180 (1997) and Di Marzo, V., TRENDS NEUROSCI., 21:521-528 (1998). For example, cannabinoid receptor ligands have been shown to have pharmacological effects on the central nervous system, the immune system and the endocrine system. Consequently, there is considerable need to develop compounds that act as cannabinoid receptor (e.g., CB2 receptor) ligands.

SUMMARY OF THE INVENTION

The present invention relates to imidazopyridine and imidazopyrimidine derivatives that act as cannabinoid receptor ligands, e.g., CB2 ligands. The invention also relates to methods of preparing the compounds, compositions containing the compounds, and to methods of treatment using the compounds.

DETAILED DESCRIPTION OF THE INVENTION

In one aspect, the present invention relates to compounds of formulas I, II, III or IV:

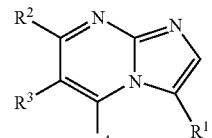

I

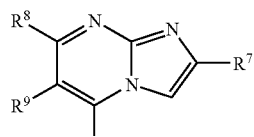

II

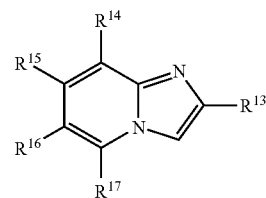

III

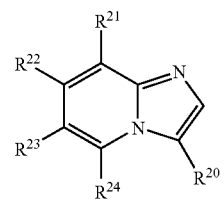

IV wherein $R^1$ is aryl or heteroaryl;

$R^2$, $R^3$ and $R^4$ are each independently hydrogen, halogen, hydroxyl, cyano, nitro, amino, alkylamino, dialkylamino, carboxyl, alkyl, halogenated alkyl, alkenyl, alkynyl, aryl, arylalkyl, heteroaryl, heteroarylalkyl, heterocycle, heterocyclealkyl, cycloalkyl, aroyl, acyl, alkoxy, aryloxy, alkythio, arylthio, alkoxycarbonyl, aryloxycarbonyl, or —C(O)NR$^5$R$^6$, wherein at least one of $R^2$ and $R^3$ is —C(O)NR$^5$R$^6$;

$R^5$ and $R^6$ are each independently hydrogen, alkyl, alkenyl, alkynyl, cycloalkyl, cycloalkylalkyl, aryl, arylalkyl, heteroaryl, heteroaryl, heterocycle, heterocyclealkyl;

$R^7$ is aryl or heteroaryl;

$R^8$, $R^9$ and $R^{10}$ are each independently hydrogen, halogen, hydroxyl, cyano, nitro, amino, alkylamino, dialkylamino, carboxyl, alkyl, halogenated alkyl, alkenyl, alkynyl, aryl, arylalkyl, heteroaryl, heteroarylalkyl, heterocycle, heterocyclealkyl, cycloalkyl, aroyl, acyl, alkoxy, aryloxy, alkythio, arylthio, alkoxycarbonyl, aryloxycarbonyl, or —C(O)NR$^{11}$R$^{12}$, wherein at least one of $R^8$ and $R^9$ is —C(O)NR$^{11}$R$^{12}$, $R^{11}$ and $R^{12}$ are each independently hydrogen, alkyl, alkenyl, alkynyl, cycloalkyl, cycloalkylalkyl, aryl, arylalkyl, heteroaryl, heteroaryl, heterocycle, heterocyclealkyl;

$R^{13}$ is aryl or heteoaryl;

$R^{14}$, $R^{15}$, $R^{16}$ and $R^{17}$ are each independently hydrogen, halogen, hydroxyl, cyano, nitro, amino, alkylamino, dialkylamino, carboxyl, alkyl, halogenated alkyl, alkenyl, alkynyl, aryl, arylalkyl, heteroaryl, heteroarylalkyl, heterocycle, heterocyclealkyl, cycloalkyl, aroyl, acyl, alkoxy, aryloxy, alkythio, arylthio, alkoxycarbonyl, aryloxycarbonyl, or —C(O)NR$^{18}$R$^{219}$, wherein at least one of $R^{15}$ and $R^{16}$ is —C(O)NR$^{18}$R$^{19}$;

R[18] and R[19] are each independently hydrogen, alkyl, alkenyl, alkynyl, cycloalkyl, cycloalkylalkyl, aryl, arylalkyl, heteroaryl, heterocycle, heterocyclealkyl;

R[20] is aryl or heteroaryl,

R[21], R[22], R[23] and R[24] are each independently hydrogen, halogen, hydroxyl, cyano, nitro, amino, alkylamino, dialkylamino, carboxyl, alkyl, halogenated alkyl, alkenyl, alkynyl, aryl, arylalkyl, heteroaryl, heteroarylalkyl, heterocycle, heterocyclealkyl, cycloalkyl, aroyl, acyl, alkoxy, aryloxy, alkythio, arylthio, alkoxycarbonyl, aryloxycarbonyl, or —C(O)NR[25]R[126], wherein at least one of R[22] and R[23] is —C(O)NR[25]R[26];

R[25] and R[26] are each independently hydrogen, alkyl, alkenyl, alkynyl, cycloalkyl, cycloalkylalkyl, aryl, arylalkyl, heteroaryl, heterocycle, heterocyclealkyl;

wherein, when present, an aryl, heteroaryl, or heterocycle group may optionally be substituted by one or more halogen, hydroxy, cyano, nitro, amino, alkylamino, dialkylamino, arylamino, diarylamino, amido, carboxyl, alkyl, halogenated alkyl, alkenyl, alkynyl, cycloalkyl, cycloalkylalkyl, aryl, arylalkyl, heteroaryl, heteroarylalkyl, heterocycle, heterocyclealkyl, aroyl, acyl, alkoxy, aryloxy, heteroaryloxy, cycloalkyloxy, cycloalkylalkyloxy, arylalkyloxy, heteroarylalkyloxy, alkythio, arylthio, alkylsulfinyl, alkylsulfonyl, arylsulfinyl, arylsulfonyl, heteroarylsulfinyl, heteroarylsulfonyl alkoxycarbonyl, aryloxycarbonyl or heteroaryloxycarbonyl, and combinations thereof;

and pharmaceutically acceptable salts or solvates (e.g., hydrates) thereof, or solvates of pharmaceutically acceptable salts thereof;

with the provisos that:
(i) R[18] and R[19] are not simultaneously hydrogen or alkyl;
(ii) when one of R[18] or R[19] is hydrogen, the other of R[18] and R[19] is not alkyl;
(iii) R[20] is other then thienyl, and
(iv) R[25] and R[26] are not simultaneously hydrogen.

In certain embodiments, the compound of Formula I is represented by subformulas Ia and Ib:

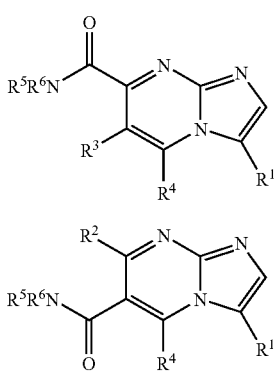

In certain embodiments, R[1] is optionally substituted aryl (e.g., optionally substituted phenyl). For example R[1] is halo-substituted phenyl, such as 2,4-dichlorophenyl, 3-chlorophenyl.

In additional embodiments, R[2] and R[3] are hydrogen, alkyl or halogenated alkyl. For example, R[2] and R[3] are hydrogen or halogenated alkyl, e.g., R[2] and R[3] are hydrogen or $CF_3$. In certain embodiments, R[2] and R[3] are $CF_3$.

In further embodiments, R[4] is hydrogen.

In certain embodiments, R[5] and R[6] are independently hydrogen, arylalkyl, heteroarylalkyl or heterocyclealkyl. For example, R[5] and R[6] are independently hydrogen or heterocyclealkyl. As a further example, one of R[5] and R[6] is hydrogen and the other of R[5] and R[6] is tetrahydropyranylmethyl (e.g., tetrahydropyran-4-ylmethyl). In another embodiment, R[5] and R[6] are not both hydrogen.

In additional embodiments of the compound of formula Ib, R[1] is aryl (e.g., optionally substituted phenyl, such as 2,4-dichlorophenyl, 3-chlorophenyl), R[2] is halogenated alkyl (e.g., $CF_3$), R[4] is hydrogen, and R[5] and R[6] are independently hydrogen or heterocyclealkyl (e.g., one of R[5] and R[6] is hydrogen and the other of R[5] and R[6] is heterocyclealkyl (e.g., tetrahydropyranylmethyl, such as tetrahydropyran-4-ylmethyl).

In certain embodiments, the compound of Formula II is represented by subformulas IIa and IIb:

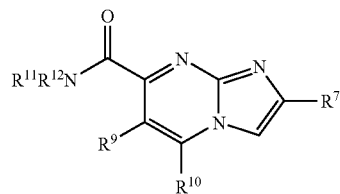

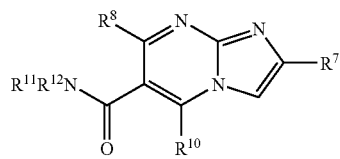

In certain embodiments, R[7] is optionally substituted aryl (e.g., optionally substituted phenyl). For example R[7] is halo-substituted phenyl, such as 2,4-dichlorophenyl, 3-chlorophenyl.

In additional embodiments, R[8] and R[9] are hydrogen, alkyl or halogenated alkyl. For example, R[8] and R[9] are hydrogen or halogenated alkyl, e.g., R[8] and R[9] are hydrogen or $CF_3$. In certain embodiments, R[8] and R[9] are $CF_3$.

In further embodiments, R[10] is hydrogen.

In certain embodiments, R[11] and R[12] are independently hydrogen, arylalkyl, heteroarylalkyl or heterocyclealkyl. For example, R[11] and R[12] are independently hydrogen or heterocyclealkyl. As a further example, one of R[11] and R[12] is hydrogen and the other of R[11] and R[12] is tetrahydropyranylmethyl (e.g., tetrahydropyran-4-ylmethyl). In another embodiment, R[11] and R[12] are not both hydrogen.

In certain embodiments, the compound of Formula III is represented by subformulas IIIa and IIIb:

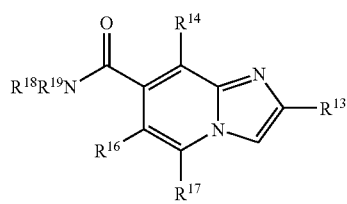

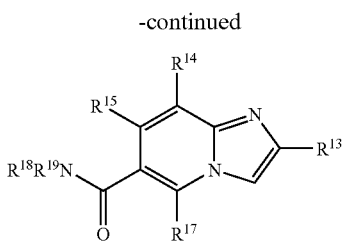

In certain embodiments, $R^{13}$ is optionally substituted aryl (e.g., optionally substituted phenyl). For example $R^{13}$ is halo-substituted phenyl, such as 2,4-dichlorophenyl, 3-chlorophenyl.

In additional embodiments, $R^{15}$ and $R^{16}$ are hydrogen, alkyl or halogenated alkyl. For example, $R^{15}$ and $R^{16}$ are hydrogen or halogenated alkyl, e.g., $R^{15}$ and $R^{16}$ are hydrogen or $CF_3$. In certain embodiments, $R^{15}$ and $R^{16}$ are hydrogen In further embodiments, $R^{14}$ and $R^{17}$ are hydrogen.

In certain embodiments, $R^{18}$ and $R^{19}$ are independently hydrogen, arylalkyl, heteroarylalkyl or heterocyclealkyl. For example, $R^{18}$ and $R^{19}$ are independently hydrogen or heterocyclealkyl. As a further example, one of $R^{18}$ and $R^{19}$ is hydrogen and the other of $R^{18}$ and $R^{19}$ is tetrahydropyranylmethyl (e.g., tetrahydropyran-4-ylmethyl).

In additional embodiments of the compound of formula IIIa, $R^{13}$ is aryl (e.g., optionally substituted phenyl, such as 2,4-dichlorophenyl, 3-chlorophenyl), $R^{14}$, $R^{16}$ and $R^{17}$ are hydrogen, and $R^{18}$ and $R^{19}$ are independently hydrogen or heterocyclealkyl (e.g., one of $R^{18}$ and $R^{19}$ is hydrogen and the other of $R^{18}$ and $R^{19}$ is heterocyclealkyl (e.g., tetrahydropyranylmethyl, such as tetrahydropyran-4-ylmethyl).

In certain embodiments, the compound of Formula IV is represented by subformulas IVa and IVb:

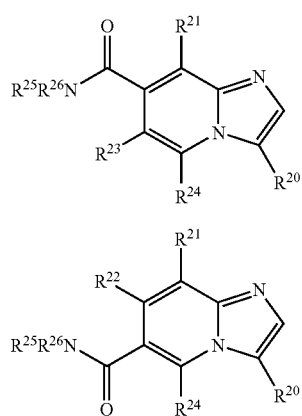

In certain embodiments, $R^{20}$ is optionally substituted aryl (e.g., optionally substituted phenyl). For example $R^{20}$ is halo-substituted phenyl, such as 2,4-dichlorophenyl, 3-chlorophenyl.

In additional embodiments, $R^{22}$ and $R^{23}$ are hydrogen, alkyl or halogenated alkyl. For example, $R^{22}$ and $R^{23}$ are hydrogen or halogenated alkyl, e.g., $R^{22}$ and $R^{23}$ are hydrogen or $CF_3$. In certain embodiments, $R^{22}$ and $R^{23}$ are hydrogen.

In further embodiments, $R^{21}$ and $R^{24}$ are hydrogen.

In certain embodiments, $R^{25}$ and $R^{26}$ are independently hydrogen, arylalkyl, heteroarylalkyl or heterocyclealkyl. For example, $R^{25}$ and $R^{26}$ are independently hydrogen or hetero-cyclealkyl. As a further example, one of $R^{25}$ and $R^{26}$ is hydrogen and the other of $R^{25}$ and $R^{26}$ is tetrahydropyranylmethyl (e.g., tetrahydropyran-4-ylmethyl).

In additional embodiments of the compound of formula IVa, $R^{20}$ is aryl (e.g., optionally substituted phenyl, such as 2,4-dichlorophenyl, 3-chlorophenyl), $R^{21}$, $R^{23}$ and $R^{24}$ are hydrogen, and $R^{25}$ and $R^{26}$ are independently hydrogen or heterocyclealkyl (e.g., one of $R^{25}$ and $R^{26}$ is hydrogen and the other of $R^{25}$ and $R^{26}$ is heterocyclealkyl (e.g., tetrahydropyranylmethyl, such as tetrahydropyran-4-ylmethyl).

In one embodiment, the present invention relates to compounds of formulas I, III or IV. In another embodiment, the present invention relates to compounds of formulas Ib, IIIa or IVa.

In certain embodiments, the compound of formulas I-IV is selected from:

3-(2,4-Dichloro-phenyl)-7-trifluoromethyl-imidazo[1,2-a]pyrimidine-6-carboxylic acid (tetrahydro-pyran-4-ylmethyl)-amide, 2-(3-Chloro-phenyl)-imidazo[1,2-a]pyridine-7-carboxylic acid (tetrahydro-pyran-4-ylmethyl)-amide, 3-(3-Chloro-phenyl)-7-trifluoromethyl-imidazo[1,2-a]pyrimidine-6-carboxylic acid (tetrahydro-pyran-4-ylmethyl)-amide, 3-(3-Chloro-phenyl)-imidazo[1,2-a]pyridine-7-carboxylic acid (tetrahydro-pyran-4-ylmethyl)-amide, and 3-(2,4-Dichloro-phenyl)-imidazo[1,2-a]pyridine-7-carboxylic acid (tetrahydro-pyran-4-ylmethyl)-amide, wherein free base forms listed above can also be in the form of a pharmaceutically acceptable salt wherein a compound listed above (in either a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof ) can also be in the form of a polymorph, and wherein if the compound exhibits chirality it can be in the form of a mixture of enantiomers such as a racemate or a mixture of diastereomers, or can be in the form of a single enantiomer or a single diastereomer.

As used herein the term "halogen" means F, Cl, Br, and I.

The term "alkyl" means a substituted or unsubstituted saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, e.g., halogen, hydroxyl, amino, alkylamino, dialkylamino, aryl, heteroaryl, alkoxy, nitro and cyano, and combinations thereof.

The term "halogenated alkyl" means a saturated hydrocarbon radical which may be straight-chain or branched-chain and may comprise about 1 to about 20 carbon atoms, for instance 1 to 12 carbon atoms, such as 1 to 8 carbon atoms, e.g., 1 to 4 carbon atoms, that is substituted by one ore more halogens, such as, but not limited to, —$CF_3$, $CF_2CF_3$, $CHF_2$, CH₂F, and the like. The use of the term "halogenated alkyl" should not be construed to mean that a "substituted alkyl" group may not be substituted by one or more halogens.

The term "alkenyl" means a substituted or unsubstituted hydrocarbon radical which may be straight-chain or branched-chain, which contains one or more carbon-carbon double bonds, and which may comprise about 1 to about 20 carbon atoms, such as 1 to 12 carbon atoms, for instance 1 to 6 carbon atoms. Suitable alkenyl groups include ethenyl, propenyl, butenyl, etc.

Substituted alkenyl groups are alkenyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

The term "alkynyl" means a substituted or unsubstituted aliphatic hydrocarbon radical which may be straight-chain or branched-chain and which contains one or more carbon-carbon triple bonds. Preferably the alkynyl group contains 2 to 15 carbon atoms, such as 2 to 12 carbon atoms, e.g., 2 to 8 carbon atoms. Suitable alkynyl groups include ethynyl, propynyl, butynyl, etc.

Substituted alkynyl groups are alkynyl groups as described above which are substituted in one or more positions by, e.g., halogen, hydroxyl, amino, carboxy, alkylamino, dialkylamino, aryl, heteroaryl, alkoxy, nitro and cyano, and combinations thereof.

The term "amino" means —NH₂.

The term "alkylamino" means —NH(alkyl), wherein alkyl is as described above.

The term "dialkylamino" means —N(alkyl)₂, wherein alkyl is as described above.

The term "aryl" means a substituted or unsubstituted aromatic monocyclic or bicyclic ring system comprising about 5 to about 14 carbon atoms, e.g., about 6 to about 10 carbon atoms. Suitable aryl groups include, but are not limited to, phenyl, naphthyl, anthracenyl.

Substituted aryl groups include the above-described aryl groups which are substituted one or more times by, for example, but not limited to, halogen, hydroxyl, amino, carboxy, alkylamino, dialkylamino, aryl, heteroaryl, alkoxy, nitro and cyano, and combinations thereof.

The term "arylamino" means —NH(aryl), wherein aryl is as described above.

The term "diarylamino" means —N(aryl)₂, wherein aryl is as described above.

The term "amido" means —CONH₂.

The term "arylalkyl" refers to an -(alkylene)-aryl group in which the aryl and alkylene portions are in accordance with the previous descriptions. Suitable examples include, but are not limited to, benzyl, 1-phenethyl, 2-phenethyl, phenpropyl, phenbutyl, phenpentyl, and napthylmethyl.

The term "carboxyl" means —C(O)OH.

The term "cycloalkyl" means a monocyclic, bicyclic or tricyclic nonaromatic saturated hydrocarbon radical having 3 to 10 carbon atoms, such as 3 to 8 carbon atoms, for example, 3 to 6 carbon atoms. Suitable cycloalkyl groups include, but are not limited to, cyclopropyl, cyclobutyl, cyclopentyl, cyclohexyl, cycloheptyl, cyclooctyl, norbornyl, 1-decalin, adamant-1-yl, and adamant-2-yl. Other suitable cycloalkyl groups include, but are not limited to, spiropentyl, bicyclo [2.1.0]pentyl, bicyclo[3.1.0]hexyl, spiro[2.4]heptyl, spiro [2.5]octyl, bicyclo[5.1.0]octyl, spiro[2.6]nonyl, bicyclo [2.2.0]hexyl, spiro[3.3]heptyl, bicyclo[4.2.0]octyl, and spiro [3.5]nonyl. Preferred cycloalkyl groups include cyclopropyl, cyclobutyl, cyclopentyl and cyclohexyl. The cycloalkyl group can be substituted, for example, by one or more halogens and/or alkyl groups.

The term "cycloalkylalkyl" means a -(alkylene)-cycloalkyl in which the cycloalkyl group is as previously described; e.g., cyclopropylmethyl, cyclobutylmethyl, cyclopentylethyl, or cyclohexylmethyl, and the like.

The term "heteroaryl" means a substituted or unsubstituted aromatic monocyclic or multicyclic ring system comprising 5 to 14 ring atoms, preferably about 5 to about 10 ring atoms and most preferably 5 or 6 ring atoms, wherein at least one of the ring atoms is an N, O or S atom. Suitable heteroaryl groups include, but are not limited to furyl, thienyl, pyrrolyl, pyrazolyl, imidazolyl, pyridyl, pyrimidinyl, benzimidazolyl, indazolyl, indolyl, quinolinyl, isoquinolinyl, naphthyridinyl and the like.

Substituted heteroaryl groups include the above-described heteroaryl groups which are substituted one or more times by, for example, halogen, hydroxyl, amino, carboxy, alkylamino, dialkylamino, aryl, heteroaryl, alkoxy, nitro and combinations thereof.

The term "heteroarylalkyl" refers to a -(alkylene)-heteroaryl group wherein the heteroaryl and alkylene portions are in accordance with the previous discussions. Suitable examples include, but are not limited to, pyridylmethyl, thiazolylmethyl, thienylmethyl, pyrimidinylmethyl, pyrazinylmethyl, and isoquinolinylmethyl, and the like.

The term "heterocycle" means a substituted or unsubstituted non-aromatic mono- or multicyclic ring system comprising 3 to 10 atoms, preferably 5 or 6, wherein at least one of the ring atoms is an N, O or S atom. Suitable heterocyle groups include, but are not limited to tetrahydrofuranyl, tetrahydrothienyl, tetrahydropyranyl, dihydropyranyl, pyrrolidinyl, piperidinyl, piperazinyl, thiomorpholinyl, morpholinyl, isoxazolinyl, and the like Substituted heterocycle groups include the above-described heterocycle groups which are substituted one or more times by, for example, halogen, amino, alkyl, hydroxy, carboxy, and combinations thereof. Heterocycle groups may also be substituted by, e.g., aryl or heteroaryl.

The term "heterocyclealkyl" refers to a -(alkylene)-heterocycle group wherein the heterocycle and alkylene portions are in accordance with the previous discussions.

The term "aroyl" means an aryl-C(O)—, in which the aryl group is as previously described. Suitable aroyl groups include, but are not limited to, benzoyl and 1-naphthoyl.

The term "acyl" means an HC(O)—, alkyl-C(O)—, cycloalkyl-C(O)—, aryl-C(O)—, or heteroalkyl-C(O)—, in which the various groups are as previously described, e.g., acetyl, propionyl, benzoyl, pyridinylcarbonyl, and the like.

The term "alkoxy" means alkyl-O— groups in which the alkyl portion is in accordance with the previous discussion. Suitable alkoxy groups include, but are not limited to, methoxy, ethoxy, n-propoxy, iso-propoxy, n-butoxy, t-butoxy, pentoxy, hexoxy, heptoxy, octoxy, and the like. For example, the alkoxy can be methoxy or ethoxy.

The term "alkenyloxy" means alkenyl-O— groups in which the alkenyl portion is in accordance with the previous discussion. Suitable alkoxy groups include, but are not limited to, —OCH₂CH=CH₂.

The term "aryloxy" means an aryl-O— group, in which the aryl group is as previously described.

The term "heteroaryloxy" means an heteroaryl-O— group, in which the heteroaryl group is as previously described.

The term "cycloalkylalkyloxy" means a —O-(alkylene)-cycloalkyl group, in which the cycloalkyl and alkylene groups are as previously described.

The term "alkylthio" means an alkyl-S— group, in which the alkyl group is as previously described.

The term "arylthio" means an aryl-S— group, in which the aryl group is as previously described.

The term "alkylsulfinyl" means a —SOR radical where R is alkyl as defined above, e.g., methylsulfinyl, ethylsulfinyl, and the like.

The term "alkylsulfonyl" means a —$SO_2R$ radical where R is alkyl as defined above, e.g., methylsulfonyl, ethylsulfonyl, and the like.

The term "arylsulfinyl" means a —SOR radical where R is aryl as defined above, e.g., phenylsulfinyl, and the like.

The term "arylsulfonyl" means a —$SO_2R$ radical where R is aryl as defined above, e.g., phenylsulfonyl, and the like.

The term "heteroarylsulfinyl" means a —SOR radical where R is heteroaryl as defined above.

The term "heteroarylsulfonyl" means a —$SO_2R$ radical where R is heteroaryl as defined above.

The term "alkoxycarbonyl" means an alkyl-O—C(O)— group, in which the alkyl group is as previously described.

The term "aryloxycarbonyl" means an aryl-O—C(O)— group, in which the aryl group is as previously described.

The term "heteroaryloxycarbonyl" means an heteroaryl-O—C(O)— group, in which the heteroaryl group is as previously described.

The term "cycloalkyloxy" means a —O-cycloalkyl group in which the cycloalkyl group is as previously described, e.g., cyclopropyloxy, cyclobutyloxy, cyclopentyloxy, cyclohexyloxy, and the like The term "arylalkyloxy" means —O-(alkylene)-aryl group, in which the aryl and alkylene groups are as previously described.

The term "heteroarylalkyloxy" means —O-(alkylene)-heteroaryl group, in which the heteroaryl and alkylene groups are as previously described.

One of ordinary skill in the art will recognize that compounds of formulas I-IV can exist in different tautomeric and geometrical isomeric forms. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of formula I can likewise be obtained by utilizing optically active starting materials in chiral synthesis processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The synthesis of radiolabeled compounds via organometallic intermediates. Tetrahedron (1989), 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

Where applicable, the present invention also relates to useful forms of the compounds as disclosed herein, such as base free forms, and pharmaceutically acceptable salts or prodrugs of all the compounds of the present invention for which salts or prodrugs can be prepared. Pharmaceutically acceptable salts include those obtained by reacting the main compound, functioning as a base with an inorganic or organic acid to form a salt, for example, salts of hydrochloric acid, sulfuric acid, phosphoric acid, methane sulfonic acid, camphor sulfonic acid, oxalic acid, maleic acid, succinic acid, citric acid, formic acid, hydrobromic acid, benzoic acid, tartaric acid, fumaric acid, salicylic acid, mandelic acid, and carbonic acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts can be prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydrobromide, a hydroformate, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of formulas I-IV can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of formulas I-IV can exist in different solvate forms. Solvates of the compounds of the invention may also form when solvent molecules are incorporated into the crystalline lattice structure of the compound molecule during the crystallization process.

The present invention also includes prodrugs of compounds of formulas I-IV. The term prodrug is intended to represent covalently bonded carriers, which are capable of releasing the active ingredient of formulas I-IV when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of formula I include compounds wherein a hydroxy, amino, carboxylic or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of formula I), amides (e.g., trifluoroacetylamino, acetylamino, and the like), and the like. Prodrugs of compounds of formulas I-IV are also within the scope of this invention.

The present invention also provides processes for preparing the compounds of formulas I-IV. For example, compounds of formula IVa may be prepared using the general reaction scheme outlined below:

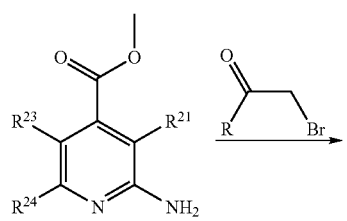

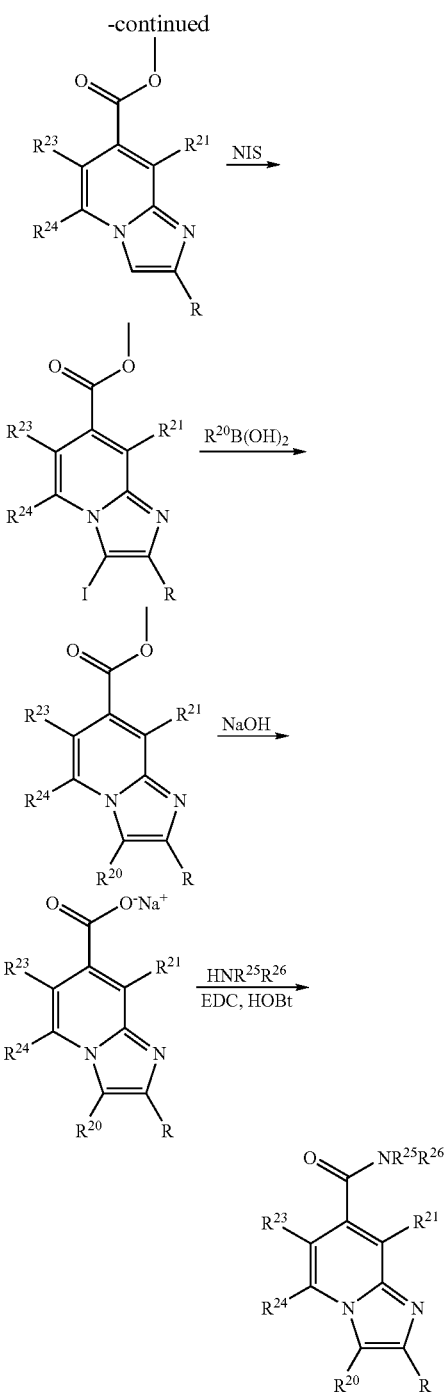

Condensation of a substituted 2-amino-isonicotinic acid methyl ester with the appropriate α:-bromo ketone or protected aldehyde affords the desired 1,2-imidazopyridine core. Regioselective iodination followed by Suzuki coupling with an aryl boronic acid provides the aryl substituted heterocycle in acceptable yields. Ester hydrolysis and subsequent amide formation under suitable conditions provides aryl substituted 1,2-imidazopyride compounds of the general formula IVa (R═H). Compounds of formula IVb may be prepared in a similar manner using the appropriately substituted nicotinic acid starting material.

As a further example, compounds of formula I (e.g., formula Ib) may be prepared using a similar procedure according to the scheme shown below:

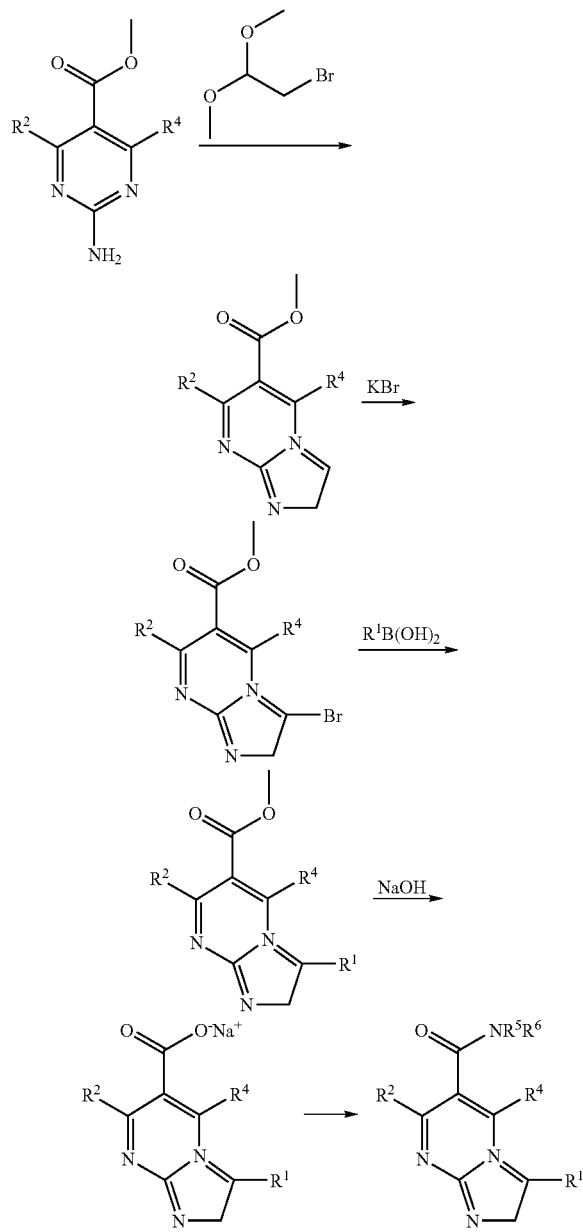

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

Administration of the compounds of the present invention may be accomplished according to patient needs, for example, orally, nasally, parenterally (subcutaneously, intraveneously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, cap lets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, past foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, the compounds according to the invention can be administered by inhalation in the form of a powder (e.g., micronized) or in the form of atomized solutions or suspensions. The aerosol formulation can be placed into a pressurized acceptable propellant.

The compounds of the present invention may be useful as cannabinoid receptor ligands. In exemplary embodiments, the compounds of the present invention may be useful as CB1 and/or CB2 receptor ligands. In preferred embodiments, the present invention the compounds of the present invention may possess preferentially high affinity for a CB2 receptor. Thus, the compounds of the present invention may be useful in the treatment of conditions that respond to cannabinoid receptor (e.g., CB2 receptor) agonists, inverse agonists and/or antagonists.

In some embodiments, the present invention provides methods for treating a condition that responds to a cannabinoid receptor (e.g., CB2 receptor) ligand. For example, some embodiments provide methods of treating a condition that responds to a cannabinoid receptor (e.g., CB2 receptor) agonist, an inverse agonist, or an antagonist comprising administering to a patient in need thereof an effective amount of a compound of the present invention.

In view of their ability to bind to the cannabinoid (e.g., CB2) receptor, the compounds of the invention may be useful in the treatment of the disorders that follow. Thus, the compounds of formula (I) may be useful as analgesics. For example they may be useful in the treatment of chronic inflammatory pain (e.g. pain associated with rheumatoid arthritis, osteo-arthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention may also be useful disease modification or joint structure preservation in multiple sclerosis, rheumatoid arthritis, osteo-arthritis, rheumatoid spondylitis, gouty arthritis and juvenile arthritis.

The compounds of the invention may be useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that precipitated them. Neuropathic pain syndromes include: diabetic neuropathy; sciatica; non-specific lower back pain; multiple sclerosis pain; fibromyalgia; HIV-related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formulas I-IV may also be useful in the treatment of fever.

The compounds of formulas I-IV may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, chronic obstructive pulmonary disease, (COPD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastro esophageal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendinitis, bursitis, and Sjogren's syndrome.

The compounds of formulas I-IV are also useful in the treatment of immunological diseases such as autoimmune diseases, immunological deficiency diseases or organ transplantation. The compounds of formulas I and II are also effective in increasing the latency of HIV infection.

The compounds of formulas I-IV are also useful in the treatment of diseases of abnormal platelet function (e.g. occlusive vascular diseases).

The compounds of formulas I-IV are also useful in the treatment of neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, motor neuron disease); vascular dementia (including multi-infarct dementia); as well as dementia associated with intracranial space occupying lesions; trauma; infections and related conditions (including HIV infection); dementia in Parkinson's disease; metabolism; toxins; anoxia and vitamin deficiency; and mild cognitive impairment associated with ageing, particularly Age Associated Memory Impairment. The compounds may also be useful for the treatment of amyotrophic lateral sclerosis (ALS) and neuroinflamation.

The compounds of formulas I-IV are also useful in neuroprotection and in the treatment of neurodegeneration following stroke, cardiac arrest, pulmonary bypass, traumatic brain injury, spinal cord injury or the like.

The compounds of formulas I-IV are also useful in the treatment of tinnitus.

The compounds of formulas I-IV are also useful in the treatment of psychiatric disease for example schizophrenia, depression (which term is used herein to include bipolar depression, unipolar depression, single or recurrent major depressive episodes with or without psychotic features, catatonic features, melancholic features, atypical features or postpartum onset, seasonal affective disorder, dysthymic disorders with early or late onset and with or without atypical features, neurotic depression and social phobia, depression accompanying dementia for example of the Alzheimer's type, schizoaffective disorder or the depressed type, and depressive disorders resulting from general medical conditions including, but not limited to, myocardial infarction, diabetes, miscarriage or abortion, etc), anxiety disorders (including generalised anxiety disorder and social anxiety disorder), panic disorder, agoraphobia, social phobia, obsessive compulsive disorder and post-traumatic stress disorder, memory disorders, including dementia, amnesic disorders and age-associated memory impairment, disorders of eating behaviours, including anorexia nervosa and bulimia nervosa, sexual dysfunction, sleep disorders (including disturbances of circadian rhythm, dyssomnia, insomnia, sleep apnea and narcolepsy), withdrawal from abuse of drugs such as of cocaine, ethanol, nicotine, benzodiazepines, alcohol, caffeine, phencyclidine (phencyclidine-like compounds), opiates (e.g. cannabis, heroin, morphine), amphetamine or amphetamine-related drugs (e.g. dextroamphetamine, methylamphetamine) or a combination thereof.

The compounds of formulas I-IV are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of formulas I-IV are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhoea) and colon cancer.

The compounds of formulas I-IV may be useful to target and kill tumors, e.g., tumors of immune origin, are thus may also be useful in the treatment of cancers of immune origin e.g., malignant lymphoblastic disease. See, e.g., Blood, 100, (2), 627-634, 2002.

The term "treating" means to relieve, alleviate, delay, reduce, reverse, improve or prevent at least one symptom of a condition in a subject. The term "treating" may also mean to arrest, delay the onset (i.e., the period prior to clinical manifestation of a disease) and/or reduce the risk of developing or worsening a condition.

An "effective amount" means the amount of a compound of formula I that, when administered to a patient (e.g., a mammal) for treating a disease, is sufficient to effect such treatment for the disease to achieve the objectives of the invention. The "effective amount" will vary depending on the compound, the disease and its severity and the age, weight, etc., of the patient to be treated.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

In some embodiments, the compounds of the present invention are administered as a mono-therapy. In other embodiments, the compounds of the present invention are administered as part of a combination therapy. For example, a compound of formulas I-IV may be used in combination with other drugs or therapies that are used in the treatment/prevention/suppression or amelioration of the diseases or conditions for which compounds of formulas I-IV are useful.

Such other drug(s) may be administered, by a route and in an amount commonly used therefor, contemporaneously or sequentially with a compound of formulas I-IV. When a compound of formula I and/or II is used contemporaneously with one or more other drugs, a pharmaceutical unit dosage form containing such other drugs in addition to the compound of formula I may be employed. Accordingly, the pharmaceutical compositions of the present invention include those that also contain one or more other active ingredients, in addition to a compound of formulas I-IV.

EXAMPLES

The present invention will now be further described by way of the following non-limiting examples. In applying the disclosure of these examples, it should be kept clearly in mind that other and different embodiments of the methods and schemes disclosed herein will no doubt suggest themselves to those of ordinary skill in the relevant art.

The following abbreviations are used herein: Ac ($CH_3CO$), DMF (dimethylformamide), EDC (1-ethyl-3-[3-dimethylaminopropyl]carbodiimide hydrochloride), HOBT (1-hydroxybenzotriazole), NIS (N-iodosuccinimide), THF (tetrahydrofuran), EtOAc (ethyl acetate), MeOH (methanol), NMR (nuclear magnetic resonance), DMSO-$d_6$ (deuterated dimethyl sulfoxide).

Procedure 1

Synthesis of 2-Amino-isonicotinic acid methyl ester

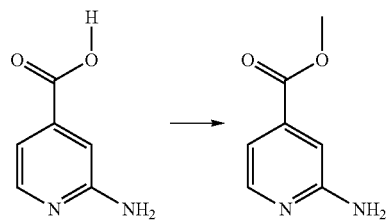

$SOCl_2$ (4 eq, 81.2 mmol) was added to a solution of aminopyridine (2.8 g, 20.3 mmol) in methanol (60 mL) at 0° C. The reaction mixture was heated at reflux for 5 hours then cooled to room temperature and concentrated to dryness. Ethyl acetate was added and removed in vacuo three times to afford crude 2-amino-isonicotinic acid methyl ester, which was used without further purification. m/z (M+H)=153.2.

Procedure 2

Synthesis of Imidazo[1,2-a]pyridine-7-carboxylic acid methyl ester

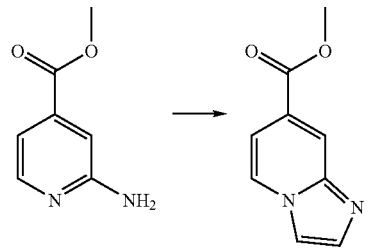

A mixture of α-bromo dimethyl acetal (3.3 g, 19.52 mmol), water (13.2 mL), and conc. HCl (0.33 mL) was heated at 80° C. for 1 hour. Solid sodium bicarbonate (1.85 g) was then added to the mixture followed by the addition of amino pyridine-ester (0.7 eq, 13.66 mmol, 2.41 g). After 2 hours at 90° C., the reaction was cooled to room temperature the product extracted with ethyl acetate. The crude mixture was purified by column chromatography (using 5-10% EtOAc-hexanes as eluent) to afford imidazo[1,2-a]pyridine-7-carboxylic acid methyl ester in 86% yield. m/z (M+H)=177.1.

Procedure 3

Synthesis of 3-Iodo-imidazo[1,2-a]pyridine-7-carboxylic acid methyl ester

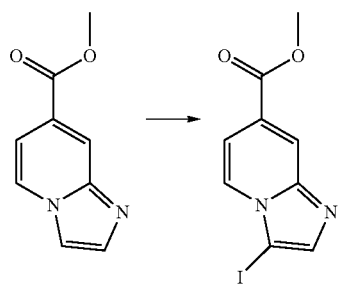

NIS (1.5 eq, 1.06 mmol, 238 mg) was added in one portion to a stirred solution of imidazo[1,2-a]pyridine-7-carboxylic acid methyl ester (0.705 mmol, 124 mg) in acetonitrile (3 mL). The resulting mixture was stirred overnight. The resulting precipitate was filtered and washed with ethyl acetate. Drying in vacuo at room temperature afforded 3-iodo-imidazo[1,2-a]pyridine-7-carboxylic acid methyl ester in 88% yield. m/z (M+H)=303.1.

Procedure 4

Synthesis of 2-(3-Chloro-phenyl)-imidazo[1,2-a]pyridine-7-carboxylic acid methyl ester

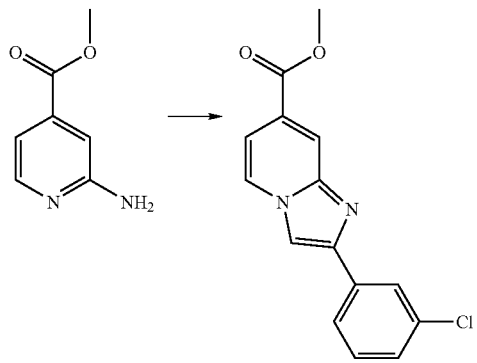

A solution of 2-amino-isonicotinic acid methyl ester (0.35 g, 1.98 mmol), meta-chlorophenyl-α-bromo ketone (1 eq., 1.98 mmol, 461 mg), Et₃N (0.3 eq, 0.59 mmol, 0.083 mL) in ethanol (10 mL) was heated at 90° C. for 5 hours. The mixture was then evaporated to dryness. Ethyl acetate was added and removed in vacuo three times to afford 515 mg (91% yield) of 2-(3-chloro-phenyl)-imidazo[1,2-a]pyridine-7-carboxylic acid methyl ester. m/z (M+H)=287.2.

Procedure 5

Synthesis of 2-(3-Chloro-phenyl)-imidazo[1,2-a]pyridine-7-carboxylic acid sodium salt

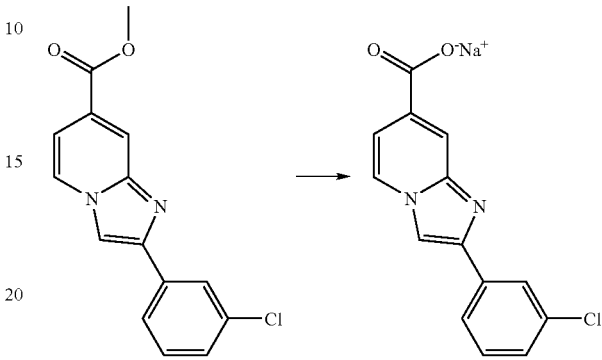

Sodium hydroxide (1 mL, 2N) was added to a solution of 2-(3-chloro-phenyl)-imidazo[1,2-a]pyridine-7-carboxylic acid methyl ester (122 mg, 0.43 mmol) in THF (4 mL) and methanol (1 mL). The mixture was stirred for 4 hours then evaporated to dryness. Ethyl acetate was added and removed in vacuo three times to afford crude 2-(3-chloro-phenyl)-imidazo[1,2-a]pyridine-7-carboxylic acid sodium salt (quantitative yield) which was used without further purification. m/z (M+H)=273.1.

Procedure 6

Synthesis of 3-Methoxy-2-(2,2,2-trifluoro-acetyl)-acrylic acid ethyl ester

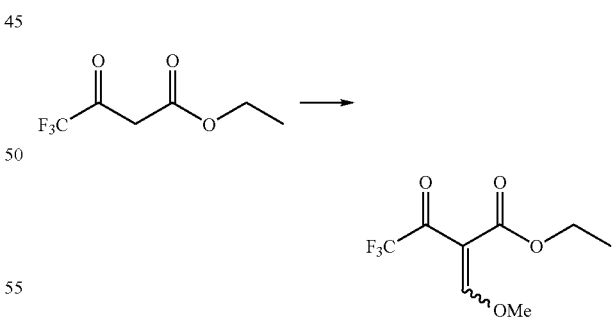

A solution 4,4,4-trifluoro-3-oxo-butyric acid ethyl ester (23.1 g, 0.13 mol), trimethyl orthoformate (2 eq, 0.251 mol, 27.5 ml), and Ac₂O (3 eq, 0.38 mol, 35.6 ml) was heated under an atmosphere of nitrogen at 120° C. for 5 hours. The solution was concentrated to afford an oil which was distilled to obtain 3-methoxy-2-(2,2,2-trifluoro-acetyl)-acrylic acid ethyl ester as the mixture of isomers (7.37 g, 26% yield after distillation). The mixture was used without further purification.

Procedure 7

Synthesis of 2-Amino-4-trifluoromethyl-pyrimidine-5-carboxylic acid ethyl ester

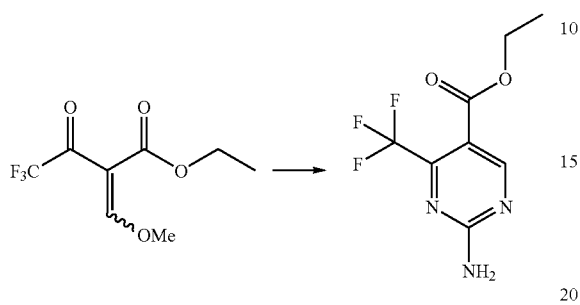

Sodium ethoxide (2 eq, 83.8 mmol, 5.7 g) was added in one portion to a solution of guanidine hydrochloride (4 g, 41.9 mmol) in absolute ethanol (100 ml) and the resulting mixture was stirred at ambient temperature for 1 hour. A dichloromethane solution of 3-methoxy-2-(2,2,2-trifluoro-acetyl)-acrylic acid ethyl ester was then added and the mixture was stirred at ambient temperature for an additional 20 hours. The solvent was then removed by evaporation, water was added to the residue, and the mixture was stirred vigorously for 2 hours then allowed to stand at room temperature. The resulting solid was isolated by filtration, washed with water then dried in vacuo to afford 6.10 g (62% yield) of 2-amino-4-trifluoromethyl-pyrimidine-5-carboxylic acid ethyl ester. m/z (M+H)=236.2.

Procedure 8

Synthesis of 7-Trifluoromehyl-imidazo[1,2-a]pyrimidine-6-carboxylic acid ethyl ester

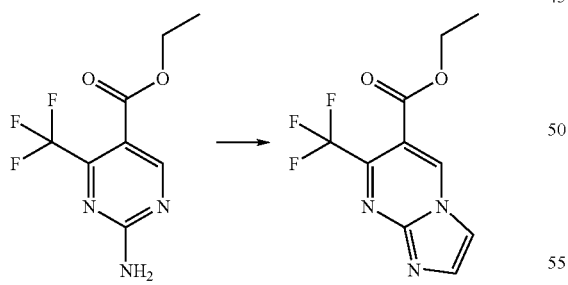

A mixture of 2-amino-pyrimidine (0.578 g, 2.46 mmol) in absolute ethanol (6 ml) was treated with bromoacetaldehyde dimethyl acetal (1.5 eq, 3.69 mmol, 0.44 ml) and hydrobromic acid (0.43 ml of a 48% aqueous solution). This mixture was then heated under reflux for 12 hours. The reaction was then cooled to ambient temperature and the solvents removed under reduced pressure. Water was removed by means of its azeotrope with toluene. The resulting solid was triturated with diethyl ether, collected by filtration and dried in vacuo to afford 7-trifluoromehyl-imidazo[1,2-a]pyrimidine-6-carboxylic acid ethyl ester as the hydrobromide salt (quantitative yield). m/z (M+H)=260.2.

Procedure 9

Synthesis of 3-Bromo-7-trifluoromehyl-imidazo[1,2-a]pyrimidine-6-carboxylic acid ethyl ester Potassium bromide (26.4 mg) and sodium acetate (2.5 eq, 6.6 mmol, 541 mg) were added sequentially to 7-trifluoromehyl-imidazo[1,2-a]pyrimidine-6-carboxylic acid ethyl ester (0.684 g, 2.64 mmol) in methanol (5.5 mL) and the resulting mixture was stirred at room temperature for 30 minutes. The mixture was then cooled to −5° C. and bromine (1.02 eq, 0.138 mL) was added. Once addition was complete, the reaction was stirred for 1 hour. The mixture was then treated with a saturated aqueous solution of sodium bisulphite and, after stirring for 5 minutes, the solvents were removed under reduced pressure. Water was added to the residue and the pH adjusted with sodium hydroxide until just basic. The resulting solid was collected by filtration, washed with ether and crystallized from hot methanol to afford 3-bromo-7-trifluoromehyl-imidazo[1,2-a]pyrimidine-6-carboxylic acid ethyl ester in quantitative yield. m/z (M+H)=339.2.

Procedure 10

Synthesis of 3-(3-Chloro-phenyl)-7-trifluoromehyl-imidazo[1,2-a]pyrimidine-6-carboxylic acid ethyl ester

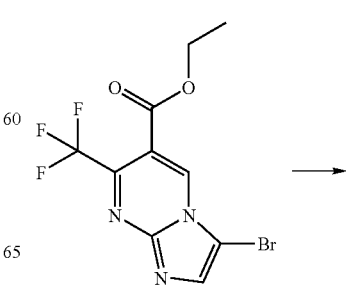

-continued

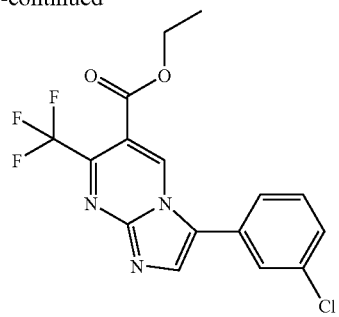

3-bromo-pyrimidine ester (125 mg, 0.37 mmol), sodium carbonate (2 eq, 0.74 mmol, 78 mg) and 3-chloro-phenyl boronic acid (1.1 eq, 0.41 mmol, 64 mg) were dissolved in toluene (3 mL) and water (1.3 mL) and the mixture was degassed with nitrogen for 15 minutes. Tetrakis(triphenylphosphine-palladium(0)) (0.05 eq, 0.019 mmol, 21 mg) was added and the mixture heated at 95° C. for 5 hours. The mixture was allowed to cool to room temperature, diluted with water and saturated sodium bicarbonate, then extracted with ethyl acetate. The organic layers were combined and dried and the product purified by column chromatography (using ethyl acetate/hexanes (1:10) as eluent) to afford 3-(3-chloro-phenyl)-7-trifluoromehyl-imidazo[1,2-a]pyrimidine-6-carboxylic acid ethyl ester (52% yield). m/z (M+H)=370.2.

Procedure 11

Synthesis of 3-(2,4-Dichloro-phenyl)-7-trifluoromehyl-imidazo[1,2-a]pyrimidine-6-carboxylic acid ethyl ester

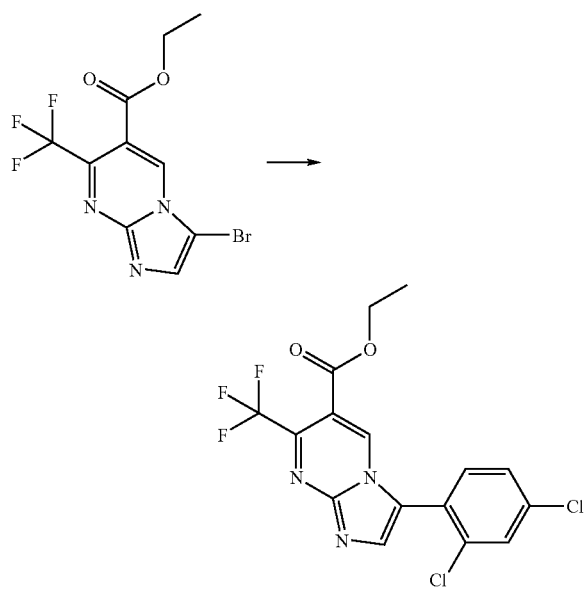

3-bromo-pyrimidine ester (95 mg, 0.28 mmol), sodium carbonate (2 eq, 0.56 mmol, 60 mg) and 2,4-dichloro phenyl boronic acid (1.1 eq, 0.309 mmol, 60 mg) were dissolved in toluene (2.5 mL), water (1.0 mL) and the mixture degassed with nitrogen for 15 min. Tetrkis(triphenylphosphine-palladium(0)) (0.05 eq, 16 mg) was added and the mixture heated at 95° C. for 5 hours. The mixture was allowed to cool to room temperature, diluted with water and saturated sodium bicarbonate, then extracted with ethyl acetate. The organic layers were combined and dried and the product purified by column chromatography (using ethyl acetate/hexanes (1:10) as eluent) to afford 3-(2,4-dichloro-phenyl)-7-trifluoromehyl-imidazo[1,2-a]pyrimidine-6-carboxylic acid ethyl ester (47% yield). m/z (M+H)=404.1.

Example 1

Synthesis of 3-(2,4-Dichlorophenyl)-7-trifluoromethyl-imidazo[1,2-a]pyrimidine-6-carboxylic acid (tetrahydro-pyran-4-ylmethyl)-amide

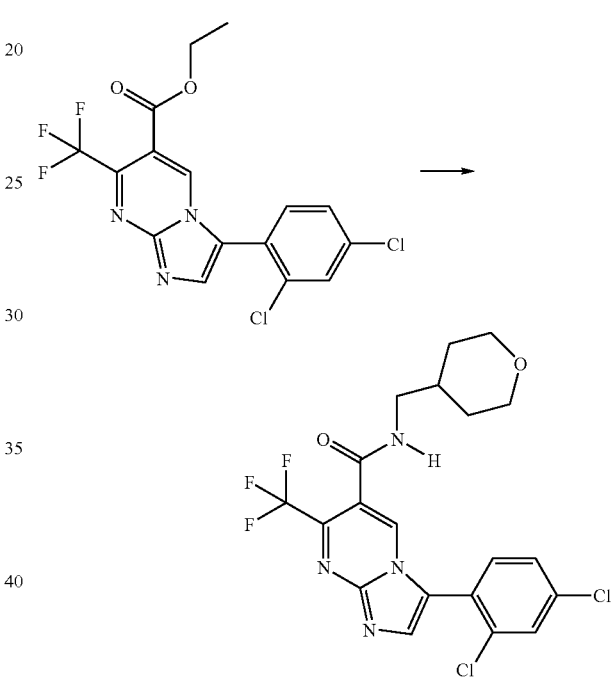

Sodium hydroxide solution (2N, 0.3 mL) was added to 3-(2,4-dichloro-phenyl)-7-trifluoromehyl-imidazo[1,2-a]pyrimidine-6-carboxylic acid ethyl ester (113 mg, 0.28 mmol) in THF (1.2 mL) and methanol (0.3 mL) at room temperature. The resulting solution was stirred for 2 hours then concentrated to dryness. Ethyl acetate was added and removed in vacuo three times. The crude residue was diluted in DMF (1.5 mL) and EDC (3 eq, 0.84 mmol, 162 mg), HOBt (3 eq, 0.843 mmol, 114 mg) were added. The mixture was stirred for 15 minutes, then tetrahydropyran-methylamine (1.5 eq, 55 mg) and triethylamine (3 eq, 0.84 mmol, 0.12 mL) were added. The resulting mixture was stirred overnight. The reaction mixture was quenched by the addition of aqueous $NH_4Cl$ solution and the product was extracted with ethyl acetate. The crude product was purified using column chromatography (using 2% methanol/EtOAc as eluent) to afford 3-(2,4-dichlorophenyl)-7-trifluoromethyl-imidazo[1,2-a]pyrimidine-6-carboxylic acid (tetrahydro-pyran-4-ylmethyl)-amide in 43% yield. $^1$H NMR (DMSO-$d_6$) δ 11.62 (1H), 8.54

(1H), 8.62 (1H), 8.41 (1H), 7.82 (1H), 7.60 (1H), 3.94 (2H), 3.72 (2H), 3.35 (2H), 1.98 (1H), 1.56 (2H), 1.34 (2H); m/z (M+H)=474.3.

Example 2

Synthesis of 2-(3-Chlorophenyl)-imidazo[1,2-a]pyridine-7-carboxylic acid (tetrahydro-pyran-4-ylmethyl)-amide

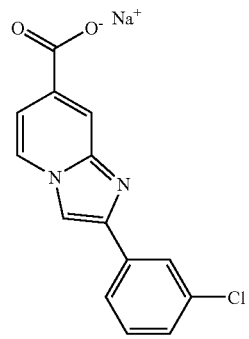

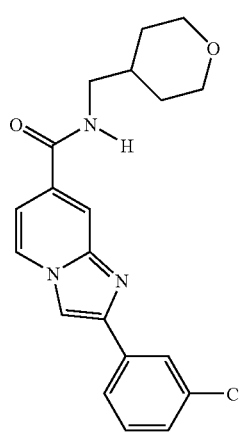

To a solution of 2-(3-chloro-phenyl)-imidazo[1,2-a]pyridine-7-carboxylic acid sodium salt (141 mg, 0.481 mmol) in DMF (2 mL) were added EDC (3 eq, 1.44 mmol, 277 mg) and HOBt (3 eq, 1.44 mmol, 195 mg). The mixture was stirred at room temperature for 15 minutes then tetrahydropyran-methylamine (1.5 eq, 0.72 mmol, 83 mg) and triethyl amine (3 eq, 1.44 mmol, 0.21 mL) were added. The reaction mixture was stirred at room temperature for 3 hours then quenched by the addition of water. The product was extracted three times with ethyl acetate and the crude product was purified by column chromatography to afford 2-(3-chloro-phenyl)-imidazo[1,2-a]pyridine-7-carboxylic acid (tetrahydro-pyran-4-ylmethyl)-amide in 65% yield. $^1$H NMR (DMSO-$_{d6}$) δ 8.69 (1H), 8.61 (2H), 8.16 (1H), 8.11 (1H), 7.98 (1H), 7.51 (1H), 7.41 (1H), 7.38 (1H), 3.92 (2H), 3.18 (2H), 3.11 (2H), 1.95 (1H), 1.31 (2H), 1.12 (2H); m/z (M+H)=370.3

Example 3

Synthesis of 3-(3-Chloro-phenyl)-7-trifluoromehyl-imidazo[1,2-a]pyrimidine-6-carboxylic acid (tetrahydro-pyran-4-ylmethyl)-amide

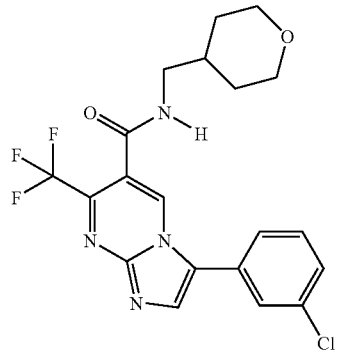

Sodium hydroxide solution (2N, 0.4 mL) was added to 3-(3-chlorophenyl)-7-trifluoromehyl-imidazo[1,2-a]pyrimidine-6-carboxylic acid ethyl ester (137 mg, 0.370 mmol) in THF (1.6 mL) and methanol (0.4 mL) at room temperature. The resulting solution was stirred for 2 hours then concentrated to dryness. Ethyl acetate was added and removed in vacuo three times. The crude residue was diluted in DMF (1.5 mL) and EDC (3 eq, 1.11 mmol, 213 mg), HOBt (3 eq, 1.11 mmol, 150 mg) were added. The mixture was stirred for 15 minutes, then tetrahydropyran-methylamine (1.5 eq, 64 mg) and triethyl amine (3 eq, 1.11 mmol, 0.16 mL) were added. The resulting mixture was stirred overnight. The reaction mixture was quenched by the addition of aqueous NH$_4$Cl solution and the product was extracted with ethyl acetate. The crude product was purified using column chromatography (using 2% methanol/EtOAc as eluent) to afford 3-(3-chlorophenyl)-7-trifluoromehyl-imidazo[1,2-a]pyrimidine-6-carboxylic acid (tetrahydro-pyran-4-ylmethyl)-amide in 43% yield. $^1$H NMR (DMSO-$_{d6}$) δ 11.65 (1H), 8.50-8.52 (2H), 8.19 (1H), 8.01 (1H), 7.48 (1H), 7.41 (1H), 3.92 (2H), 372 (2H), 3.31 (2H), 1.92 (1H), 1.58 (2H), 1.31 (2H); m/z (M+H)= 439.3.

Example 4

Synthesis of 3-(3-Chloro-phenyl)-imidazo[1,2-a]pyridine-7-carboxylic acid (tetrahydro-pyran-4-ylmethyl)-amide

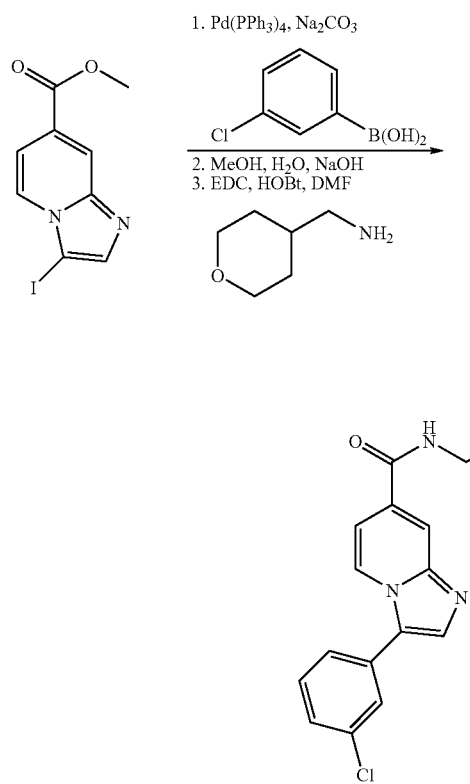

A mixture of 3-iodo-imidazo[1,2-a]pyridine-7-carboxylic acid methyl ester (230 mg, 0.76 mmol), Pd(PPh$_3$)$_4$ (44 mg, 0.038 mmol), Na$_2$CO$_3$ (161 mg, 1.52 mmol) and 3-chlorophenylboronic acid (131 mg, 0.84 mmol) was heated at reflux for 1 hour. The mixture was then allowed to cool and concentrated in vacuo. The residue was dissolved in MeOH (25 mL) and water (25 mL) and 50% NaOH (5 mL) was added. The mixture was allowed to stir at room temperature for 15 hours then concentrated in vacuo. The mixture was triturated with ethyl acetate (20 mL) and the resulting solid was filtered to afford 3-(3-chloro-phenyl)-imidazo[1,2-a]pyridine-7-carboxylic acid sodium salt (100 mg, 58%) The mixture was dissolved in DMF (2 mL) and EDC (100 mg, 0.52 mmol) and HOBt (70 mg, 0.52 mmol) were added. The mixture was allowed to stir for 10 minutes and 4-aminomethyltetrahydropyran (0.075 mL, 0.52 mmol) was added. The mixture was stirred for 2 hours then poured into water (15 mL) and the product extracted with ethyl acetate (2×50 mL). The combined organic layers were dried over anhydrous sodium sulfate and concentrated in vacuo to afford 3-(3-chlorophenyl)-imidazo[1,2-a]pyridine-7-carboxylic acid (tetrahydro-pyran-4-ylmethyl)-amide. $^1$H NMR (DMSO-$d_6$) δ 8.75 (1H), 8.65 (1H), 8.25 (1H), 8.00 (1H), 7.80 (1H), 7.70 (1H), 7.60 (1H), 7.52 (1H), 7.41 (1H), 3.85 (2H), 3.32 (2H), 3.20 (2H), 1.83 (1H), 1.60 (2H), 1.22 (2H); m/z (M+H)=370.05.

Example 5

Synthesis of 3-(2,4-Dichloro-phenyl)-imidazo[1,2-a]pyridine-7-carboxylic acid (tetrahydro-pyran-4-ylmethyl)-amide

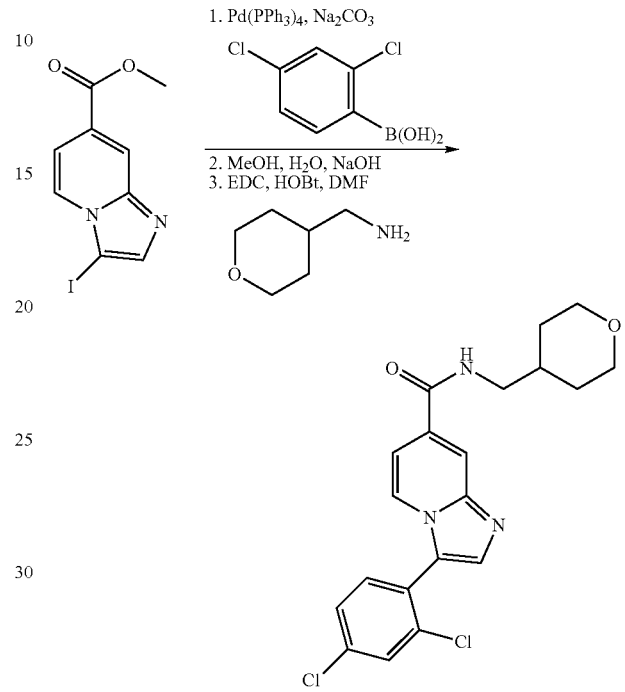

A mixture of 3-iodo-imidazo[1,2-a]pyridine-7-carboxylic acid methyl ester (230 mg, 0.76 mmol), Pd(PPh$_3$)$_4$ (44 mg, 0.038 mmol), Na$_2$CO$_3$ (161 mg, 1.52 mmol), 2,4-dichlorophenylboronic acid (160 mg, 0.84 mmol) was heated at reflux for 1 hour. The mixture was then allowed to cool and concentrated in vacuo. The residue was dissolved in MeOH (25 mL) and water (25 mL) and 50% NaOH (5 mL) was added. The mixture was allowed to stir at room temperature for 15 hours then concentrated in vacuo. The mixture was triturated with ethyl acetate (20 mL) and the resulting solid was filtered to afford 3-(2,4-dichloro-phenyl 1)-imidazo[1,2-a]pyridine-7-carboxylic acid sodium salt (47 mg, 19%) The mixture was dissolved in DMF (2 mL) and EDC (33 mg, 0.17 mmol) and HOBt (23 mg, 0.17 mmol) were added. The mixture was stirred for 10 minutes, then 4-aminomethyltetrahydropyran (0.025 mL, 0.17 mmol) and Et$_3$N (0.040 mL, 0.28 mmol) were added. The mixture was stirred for 2 hours then poured into water (15 mL). The precipitate was filtered to afford 11 mg (20% yield) of 3-(2,4-dichloro-phenyl)-imidazo[1,2-a]pyridine-7-carboxylic acid (tetrahydro-pyran-4-ylmethyl)-amide $^1$H NMR (DMSO-$d_6$) δ 8.72 (1H), 8.35 (1H), 8.15 (1H), 7.90 (2H), 7.55 (2H), 7.40 (1H), 3.80 (2H), 3.26 (2H), 3.23 (2H), 1.80 (1H), 1.60 (2H), 1.25 (2H); m/z (M+H)= 370.05.

Competition Binding Assay (96 Well Filtration)

3H-CP-55940 (Perkin-Elmer, NET-1051) was selected and used as the radio-labelled tracer for this study. CP55940 (Tocris, 0949) was selected and used as the unlabelled competitors for this study.

Materials

Assay buffer: 50 mM Tris-HCl pH 7.4, 2.5 mM EDTA, 0.5% protease free BSA

Filtration buffer: 50 mM Tris-HCl pH 7.4, 2.5 mM EDTA, 0.5% protease free BSA

Membranes: Thawed on ice and diluted to give 10 μg/ml (0.2 μg/20 μl), kept on ice.

Radioligand: [$^3$H]CP 55,940 (Perkin Elmer, NET-1051, 160.6 Ci/mmol), diluted in assay buffer to give 1.61 μCi/ml, ~89133 dpm/25 μl. Final assay concentration 1.0 nM.

Ligand: CP 55,940 (Tocris, 0949), diluted in assay buffer.

Filters: GF/B Unifilter plate (Perkin Elmer, 6005177) pre-soaked in 0.5% PEI for 2h at RT.

Assay Procedure

180 μl of assay buffer (205 μl for total binding determination), 25 μl of ligand at increasing concentrations, 25 μl of radioligand, 20 μl of membrane extracts (0.2 μg) were added successively in the wells of a 96-well plate (Master Block, Greiner, 786201) and incubated 60 min at 30° C. in a water bath. This was then filtered over GF/B filters with a Filtermate Harvester (Perkin Elmer) and the filters were washed six times with 0.5 ml of ice-cold filtration buffer. 50 μl of Microscint 20 (Packard) was added, incubated 15 min on an orbital shaker and counted with a TopCount™ or MicroBeta™ for 1 min/well.

The compounds of the present invention typically show binding activities of >50% at 20 μM concentration.

The entire disclosures of all applications, patents and publications, cited above and below, are hereby incorporated by reference.

While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalence in all respects.

What is claimed is:

1. A compound of formula I:

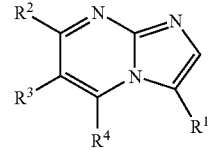

wherein $R^1$ is aryl or heteroaryl;

$R^2$, $R^3$ and $R^4$ are each independently hydrogen, halogen, hydroxyl, cyano, nitro, amino, alkylamino, dialkylamino, carboxyl, alkyl, halogenated alkyl, alkenyl, alkynyl, aryl, arylalkyl, heteroaryl, heteroarylalkyl, heterocycle, heterocyclealkyl, cycloalkyl, aroyl, acyl, alkoxy, aryloxy, alkylthio, arylthio, alkoxycarbonyl, aryloxycarbonyl, or —C(O)NR$^5$R$^6$, wherein at least one of $R^2$ and $R^3$ is —C(O)NR$^5$R$^6$;

$R^5$ and $R^6$ are each independently hydrogen, alkyl, alkenyl, alkynyl, cycloalkyl, cycloalkylalkyl, aryl, arylalkyl, heteroaryl, heteroaryl, heterocycle, or heterocyclealkyl;

and pharmaceutically acceptable salts thereof.

2. A compound according to claim 1, wherein $R^1$ is aryl.

3. A compound according to claim 2, wherein $R^1$ is optionally substituted phenyl.

4. A compound according to claim 3, wherein $R^1$ is 3-chlorophenyl or 2,4-dichlorophenyl.

5. A compound according to claim 3, wherein $R^3$ is —C(O)NR$^5$R$^6$.

6. A compound according to claim 5, wherein $R^5$ and $R^6$ are independently hydrogen or heterocyclealkyl.

7. A compound according to claim 6, wherein $R^5$ is hydrogen and $R^6$ is tetrahydropyranylmethyl.

8. A compound according to claim 5, wherein $R^2$ is halogenated alkyl.

9. A compound according to claim 1 chosen from:

3-(2,4-Dichloro-phenyl)-7-trifluoromethyl-imidazo[1,2-a]pyrimidine-6-carboxylic acid (tetrahydro-pyran-4-ylmethyl)-amide, and 3-(3-Chloro-phenyl)-7-trifluoromethyl-imidazo[1,2-a]pyrimidine-6-carboxylic acid (tetrahydro-pyran-4-ylmethyl)-amide, and pharmaceutically acceptable salts thereof.

10. A pharmaceutical composition comprising a compound according to claim 1 and a pharmaceutically acceptable carrier.

* * * * *